US00PP27256P3

(12) United States Plant Patent
Probasco et al.

(10) Patent No.: US PP27,256 P3
(45) Date of Patent: Oct. 11, 2016

(54) HOP PLANT NAMED 'HBC 564'

(50) Latin Name: *Humulus lupulus*
Varietal Denomination: HBC 564

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Jop Breeding Company, LLC., Yakima, WA (US)

( * ) Notice: Subject to any disclaimer, the term of this patent is extended or adjusted under 35 U.S.C. 154(b) by 190 days.

(21) Appl. No.: 13/998,587

(22) Filed: Nov. 13, 2013

(65) Prior Publication Data

US 2015/0135376 P1 May 14, 2015

(51) Int. Cl.
*A01H 5/00* (2006.01)

(52) U.S. Cl.
USPC ..... Plt./236

(58) Field of Classification Search
USPC ..... Plt./236
CPC ..... A01H 5/00
See application file for complete search history.

*Primary Examiner* — Kent L Bell
(74) *Attorney, Agent, or Firm* — Ballew Law

(57) ABSTRACT

A new hop plant named 'HBC 564' is disclosed. The cones of 'HBC 564' mature in mid-September, and yield a crop of 2200 to 2600 pounds per acre. 'HBC 564' is used for its very unique aromatic quality, high alpha acid content and exceptional yield.

6 Drawing Sheets

Genus and species: *Humulus lupulus*.
Variety denomination: 'HBC 564'.

CROSS-REFERENCE TO RELATED APPLICATIONS

None

STATEMENT REGARDING FEDERALLY SPONSORED RESEARCH OR DEVELOPMENT

None

BACKGROUND OF THE INVENTION

'HBC 564' is a product of a controlled breeding program carried out by the inventors in the Yakima Valley of Washington state. 'HBC 564' was one of several seedlings resulting from a cross made in 2007 of female parent 'Tillicum' (patented) and male parent 'HBC 20-9-10' (not patented). A single plant of 'HBC 564' was discovered in 2010 and used in a brewing trial during the winter of 2010-2011. Based on the preliminary brewing trial, 'HBC 564' was expanded in the Toppenish, Wash. by means of asexual propagation by softwood cutting in 2011, and those plants were planted in a one acre block in the Toppenish, Wash. area to test large scale growing, brewing and solvent extraction beginning with the 2012 crop. Through several generations of asexual propagation by softwood cuttings at a greenhouse facility in Yakima, Wash. 'HBC 564' has been observed to retain its distinctive characteristics and remain true to type.

BRIEF DESCRIPTION OF THE PHOTOGRAPH

Figure 1:
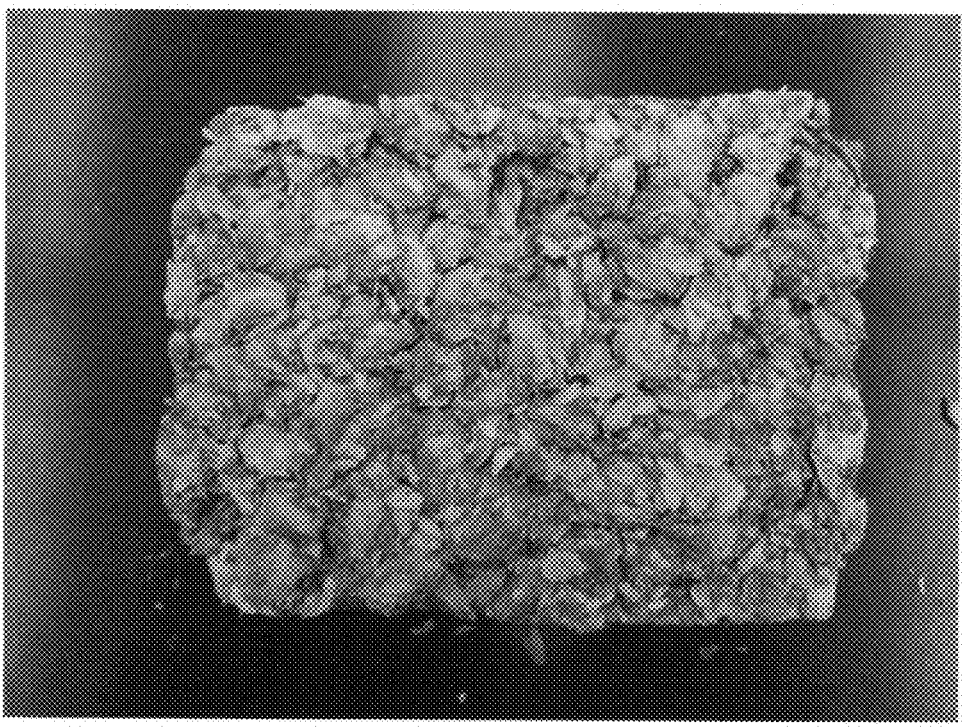
FIG. 1 illustrates the dried and pressed hop cones of 'HBC 564'.
Figure 2:
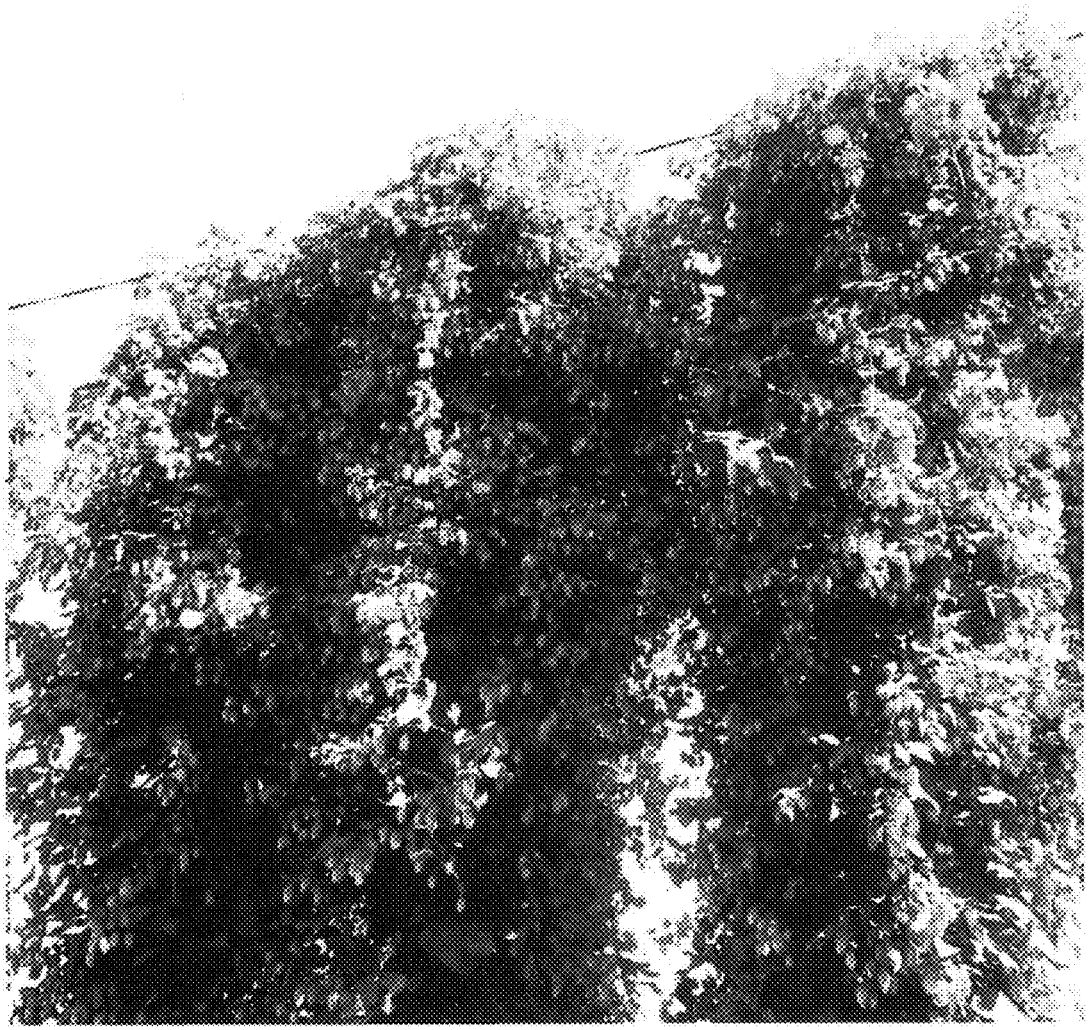
FIG. 2 illustrates mature 'HBC 564' hop plants grown on a trellis.
Figure 3:
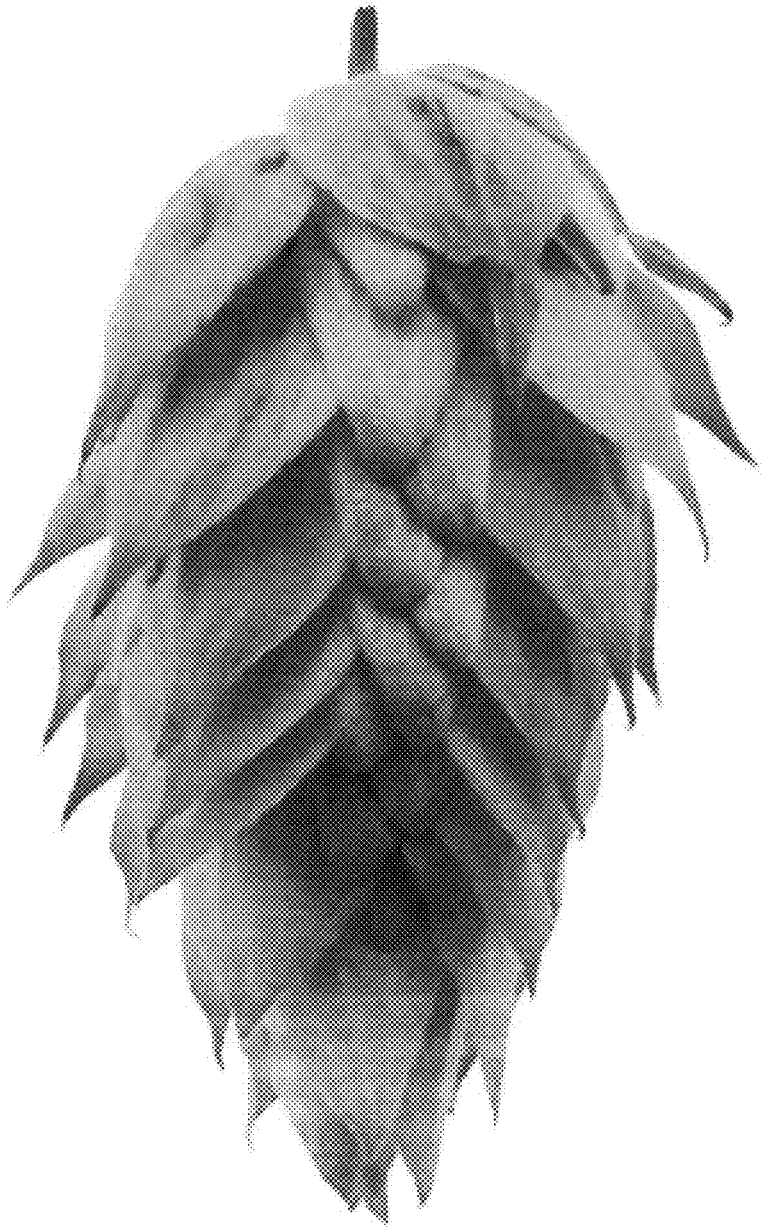
FIG. 3 illustrates a mature whole hop cone of a mature 'HBC 564' hop plant.
Figure 4:
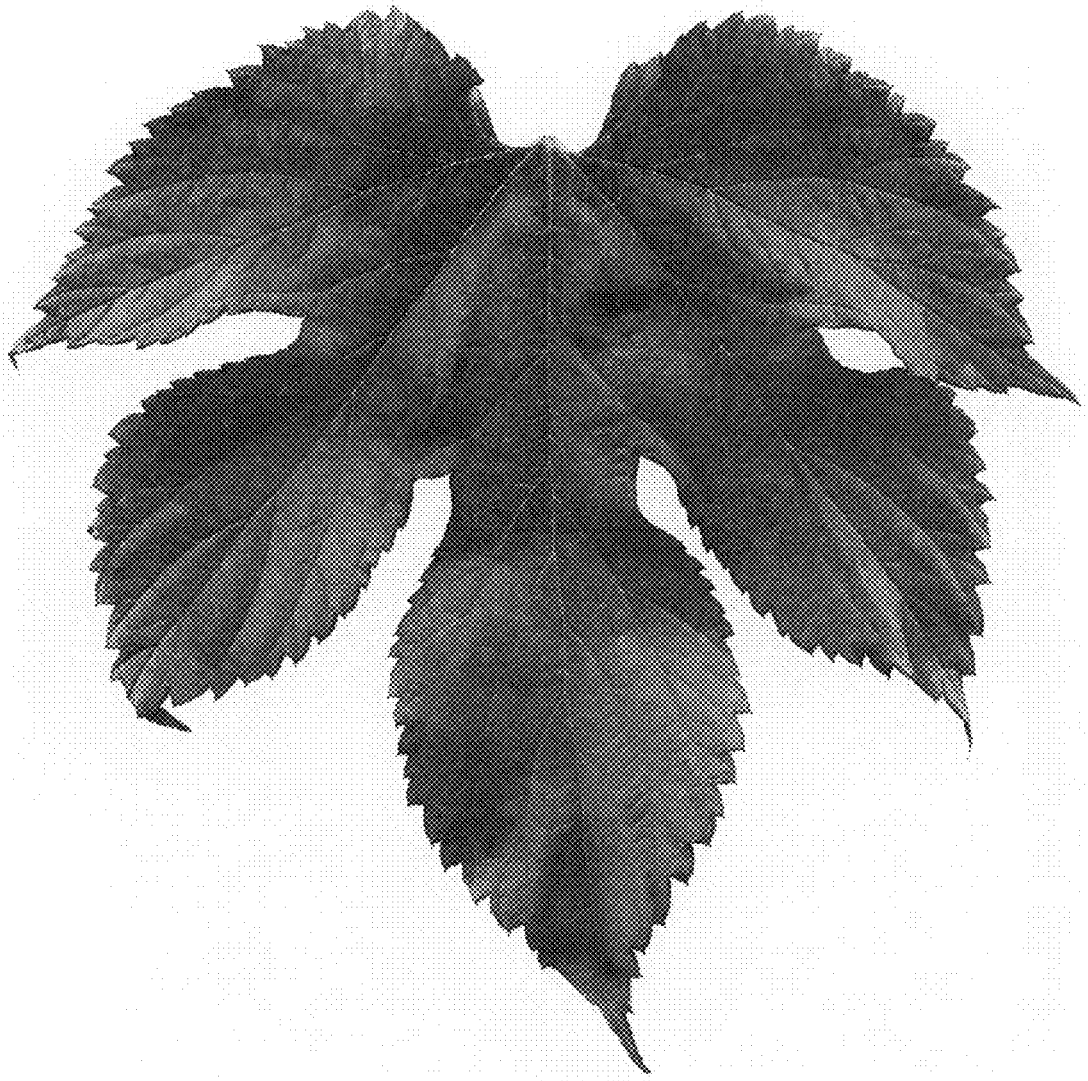
FIG. 4 illustrates a leaf from a mature 'HBC 564' hop plant.
Figure 5:
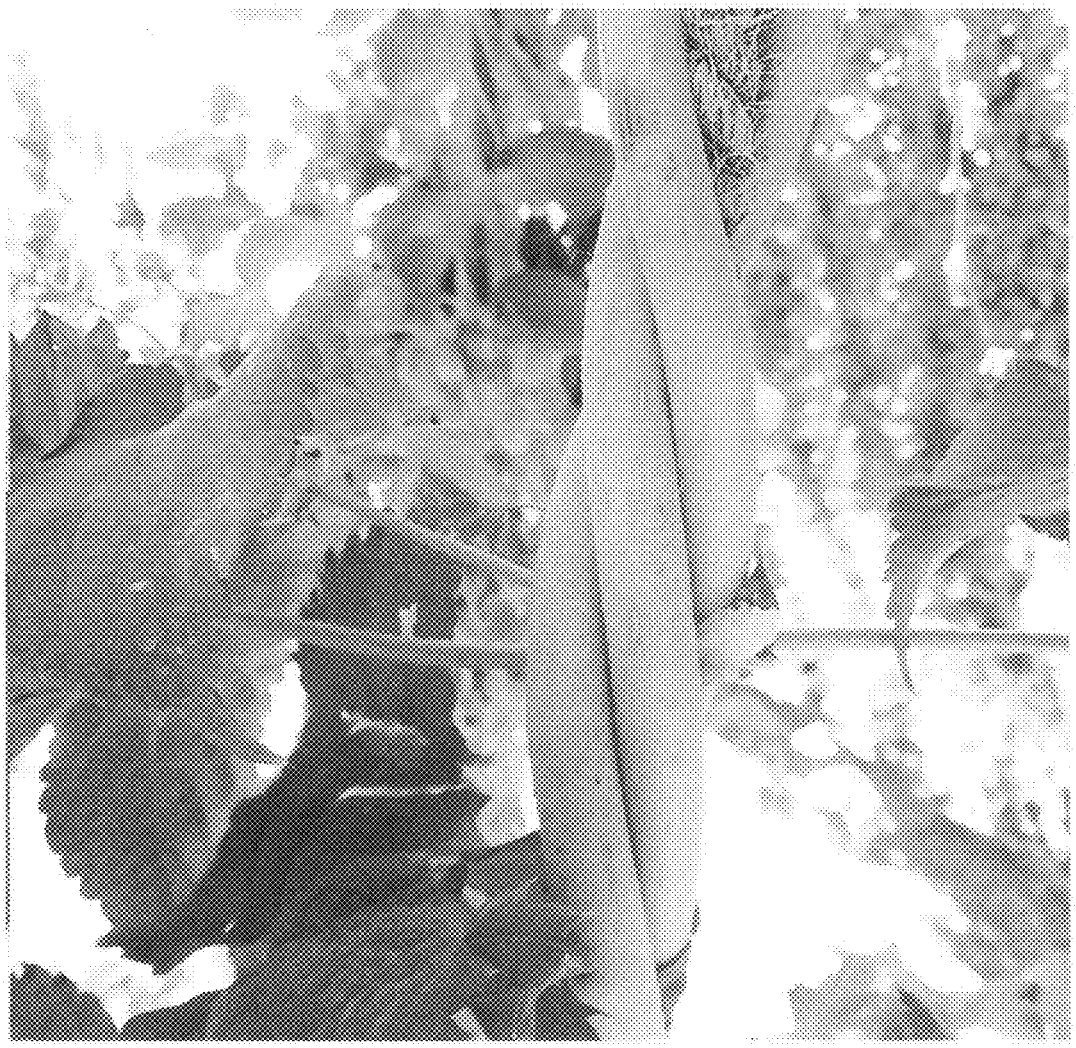
FIG. 5 illustrates the bine of a mature 'HBC 564' hop plant.
Figure 6:
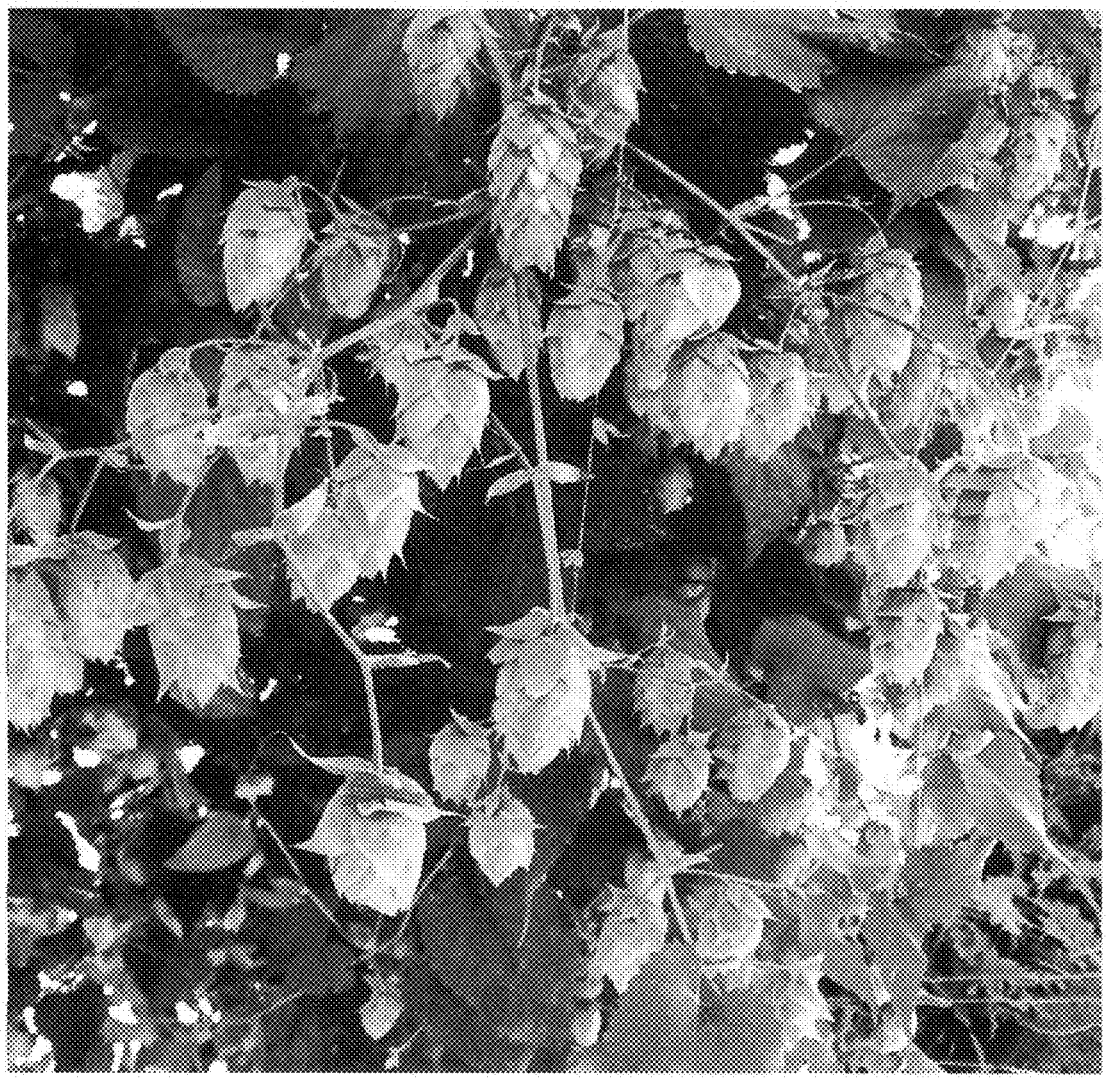
FIG. 6 illustrates the cones and leaves of a mature 'HBC 564' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2012 growing season at Toppenish, Wash.

'HBC 564' is distinguishable from its parent plants ('Tilicum' and 'HBC 20-9-10'). 'HBC 564' is distinguishable from its male parent 'HBC 20-9-10' with flowers that develop into mature hop cones without producing pollen, while flowers of 'HBC 564' produce pollen without developing into mature hop cones.

Table 1. sets forth some of the distinguishing characteristics of 'HBC 564' as compared to its female parent 'Tilicum' and to 'HBC 394' (U.S. Plant Pat. No. 21,289):

| Characteristic | 'Tillicum' | 'HBC 564' | 'HBC 394' |
|---|---|---|---|
| Humulene Content of Oil (%) | 14.0 | 28.0 | 24.0 |
| Caryophylene Content of Oil (%) | 7.4 | 14.0 | 8.0 |

-continued

| Characteristic | 'Tillicum' | 'HBC 564' | 'HBC 394' |
|---|---|---|---|
| Beta Acids Content of Cone (%) | 9.5-11.5 | 7.5-9.5 | 4.5-5.5 |
| Ploidy Condition | Diploid (but made tetraploid through application of colchicine) | Triploid | Diploid |

It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, provided by The Royal Horticultural Society of Great Britain.

Species: *Humulus lupulus*.

Ploidy: Triploid.

Use: Brewing.

Disease susceptibility: 'HBC 564' is tolerant to infestations of hop downy mildew incited by *Pseudoperonospora humuli*. 'HBC 564' is resistant to strains of hop powdery mildew found in the Yakima Valley and incited by *Podosphaera macularis*. 'HBC 564' is tolerant to *Verticilium* Wilt.

Pest susceptibility: 'HBC 564' is not resistant to normal infestations of hop aphid *Phorodon humuli* and two-spotted spider mite *Tetranychus urticae*.

Harvest date: September 9-15 (2012 growing season, Toppenish, Wash.).

Crop yield: 2200 to 2600 pounds per acre.

Plant shape: Columnar when grown on a typical 18 foot hop trellis.

Bine:

*Color*.—Yellow green 145A.
*Stipule direction*.—Up.
*Stipule color*.—Yellow green N144A.
*Avg. number stipules per bine*.—21 pairs.
*Stripe*.—Absent.
*Bine diameter*.—10.0 mm at base; 10.0 mm at 2.74 m; 7.0 mm at 5.5 m.
*Bine length*.—6.4 meters average length when grown under normal commercial conditions on a standard hop trellis.
*Length between bine internodes*.—30.5 cm average.
*Avg. lateral length*.—53 cm.
*Lateral diameter*.—5 mm at the base; 0.5 mm at the terminal end.
*Length between lateral internodes*.—12.7 cm.
*Lateral color*.—Yellow green 148C.

Leaf:

*Arrangement*.—Opposite.
*Shape*.—Cordate; Palmate lobes.
*Leaf base shape*.—Cordate.
*Average length of mature leaf*.—25.0 cm.
*Average width of mature leaf*.—18.0 cm.
*Color of mature leaf upper surface*.—Green 133A.
*Color of mature leaf lower surface*.—Green 133A.
*Color of immature leaf upper surface*.—Green 133A.
*Color of immature leaf lower surface*.—Green 133A.
*Number of lobes*.—5.
*Margin*.—Serrate.
*Serrations per inch*.—5.
*Average petiole length* (*mature*).—10.0 cm.
*Petiole diameter*.—3.0 mm at base to 2.0 mm at terminal end.
*Petiole color at base*.—Yellow green 145A.
*Petiole color at terminal end*.—Yellow green 145A.
*Venation*.—Palmate.
*Vein color*.—Green 133A.

Cone:

*Average weight*.—900 mg.
*Average length*.—3.5 cm.
*Average diameter*.—1.5 cm.
*Bract tip color*.—Green 137A.
*Bract base color*.—Green 138B.
*Bracteole color*.—Yellow green 146C.
*Cone shape*.—Oblong.
*Cone pickability*.—Easy.
*Bract shape*.—Cuspidate.
*Bract average length*.—11 mm.
*Bract average width*.—9 mm.
*Bract tip shape*.—Cuspidate.
*Bract tip position*.—Alligned.
*Bracteole shape*.—Obtuse.
*Bracteole average length*.—12 mm.
*Bracteole average width*.—7 mm.
*Lupulin gland color*.—Yellow green 150A.
*Lupulin gland shape*.—Pedunculated oblong polyps.
*Lupulin gland number*.—Medium number per cone.

Analytical characteristics:

*Alpha acid*.—15% to 16% (of cone weight).
*Beta acid*.—7.5% to 8.5% (of cone weight).
*Cohumulone*.—34% to 36% (of alpha acids).
*Humulene*.—27 to 28% (of total oils).
*Caryophyllene*.—13 to 14% (of total oils).
*Humulene/caryophyllene ratio*.—2:1.
*Myrcene*.—32 to 33% (of total oils).
*Farnesene*.—0.5% to 0.7%.
*Linalool*.—0.9% to 1.3%.
*Total oil*.—1.8 to 2.3 mL per 100 g cones.
*Storage stability*.—70% to 80% alpha acids remaining after six months storage at room temperature.

What is claimed:

1. A new and distinct hop plant as shown and described herein.

* * * * *